United States Patent [19]

Harbuck

[11] Patent Number: 4,501,263

[45] Date of Patent: Feb. 26, 1985

[54] METHOD FOR REDUCING HYPERTENSION OF A LIVER

[76] Inventor: Stanley C. Harbuck, P.O. Box 1643, Salt Lake City, Utah 84110

[21] Appl. No.: 364,139

[22] Filed: Mar. 31, 1982

[51] Int. Cl.³ .................... A61B 19/00; A61F 1/00
[52] U.S. Cl. ............................................. 128/1 R; 3/1; 3/1.4; 604/9; 604/284
[58] Field of Search .............. 3/1.4, 1, 1 A; 128/1 R; 604/8-10, 43, 284

[56] References Cited

U.S. PATENT DOCUMENTS

| | | | |
|---|---|---|---|
| 3,272,204 | 9/1966 | Artandi et al. ............... | 3/1.4 X |
| 4,204,525 | 5/1980 | Olson ........................... | 128/1 R |
| 4,208,745 | 6/1980 | Okita ............................ | 3/1.4 |
| 4,225,979 | 10/1980 | Rey et al. ..................... | 3/1 |
| 4,240,434 | 12/1980 | Newkirk ....................... | 604/9 |
| 4,311,659 | 1/1982 | Rey et al. ..................... | 3/1 X |
| 4,313,231 | 2/1982 | Koyamada .................... | 3/1.4 |

Primary Examiner—Ronald L. Frinks
Attorney, Agent, or Firm—Townsend and Townsend

[57] ABSTRACT

In an organism having a vascular system, a device and method for diverting blood flow from one blood vessel to another, such as from the hepatic artery to the portal vein for reducing hypertension of the liver. The method includes the implantation of a device according to the invention by which blood is diverted. A conduit is inserted within one vessel, normally a vein, and blood diverted to the conduit from another vessel such as an artery, wherein the blood is mixed.

2 Claims, 4 Drawing Figures

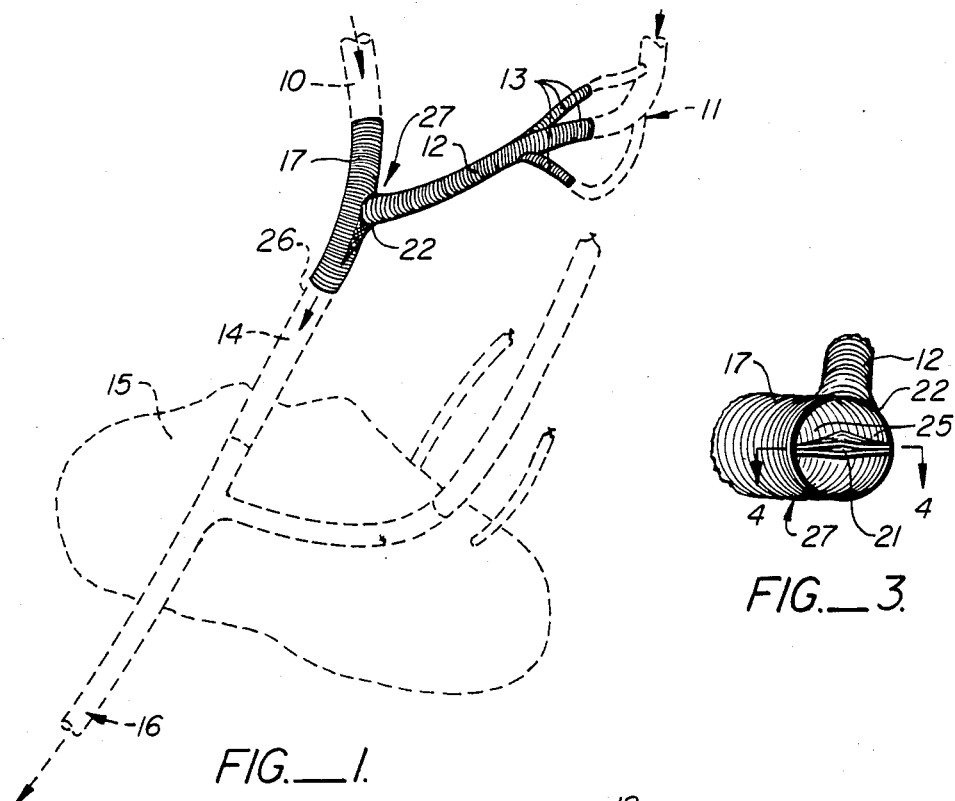
FIG._1.
FIG._3.
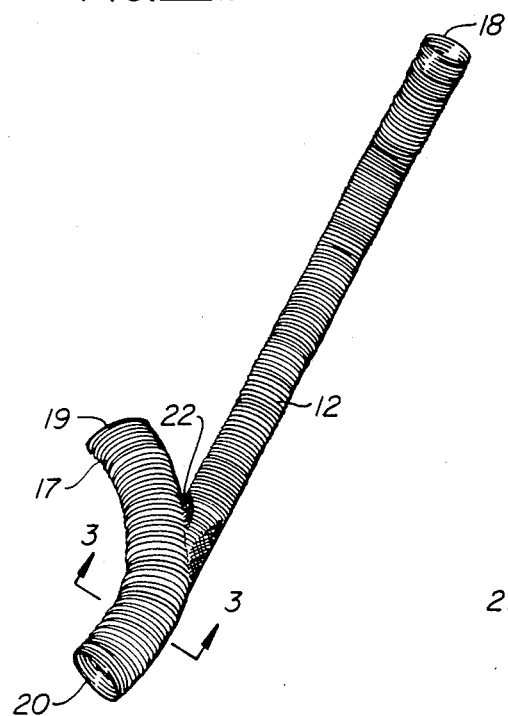
FIG._2.
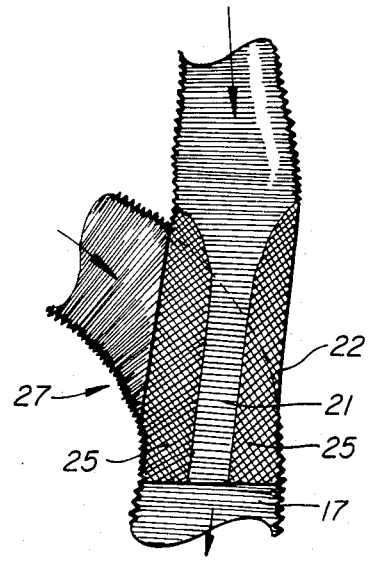
FIG._4.

4,501,263

METHOD FOR REDUCING HYPERTENSION OF A LIVER

BACKGROUND OF THE INVENTION

1. Field of the Invention

This invention relates to a surgically implantable device for use in mixing blood and for treatment of conditions such as hypertension. In particular a device according to the invention may be used to reduce hypertension of a cirrhotic liver.

The liver is connected to the vascular system through the hepatic artery and a portal vein on its proximal side and through a hepatic vein on its distal side. The hepatic artery and portal vein merge within the liver to provide the blood flow for the hepatic vein.

Hypertension of the liver, for instance in a cirrhotic liver, or in the case of hepatitis, is a serious health problem. Although there exists a pharmacology for partially treating liver hypertension, no way exists as yet for reducing the amount of work the liver must perform and allow the liver to repair itself.

In the treatment of some pathological conditions of some organs, it is desirable to alter the blood flow patterns to an organ, particularly to the liver. For example, it is believed that a high volume of arterial flow to the liver may be a block to portal flow to the liver. A blockage in portal flow to the liver is believed to cause a diversion of blood flow around the liver such that the blood from the stomach is not adequately filtered. By increasing the portal flow to the liver and/or decreasing the arterial flow to the liver, it is believed that the normal blood flow can be restored to the pathological liver, which may enable it to heal itself and to regain effectiveness.

There are various applications for a device for mixing, injecting or shunting blood flow. One such application is the so-called porta caval shunt wherein the flow of the portal vein is shunted to one of the vena cava veins.

2. Description of the Prior Art

Until now the joining of blood vessels to mix blood flow has been accomplished by surgically suturing vessels together along a longitudinal incision of one of the vessels. Unfortunately, such a technique provides only limited edge control at the junction of the joined vessels. It is therefore difficult to construct a reliable junction, and such a junction is prone to failure, particularly under pressure from blood flow. In addition, in such a technique, it is not readily possible to control the ratio of mixing of blood or the angle at which blood is injected into mixture.

In general, placing an implant in the body is well known. However, there is no decompression mechanism or similar device for handling in vivo blood flow. Arterialization of the portal vein is known wherein arterial tissue is cleaved to venous tissue and venous tissue is ligated upstream of the junction. No mixing of venous blood has been suggested.

SUMMARY OF THE INVENTION

In an organism having a vascular system, a method and device are provided for diverting blood flow from one vessel, such as the artery, to another vessel, such as the vein proximal of the liver, to mix blood, to reduce blood pressure or to otherwise alter blood flow. The method includes the implantation of a device according to the invention having a first or arterial conduit by which blood is diverted from an artery proximal of the organ and a second or vein conduit having a junction with the arterial conduit for delivery of arterial blood to the vein proximal of the organ. The vein conduit of the device is inserted within the vein proximal of the organ. Blood diverted from the artery may be mixed at a selected ratio with venous blood within the vein conduit, and the angle of injection can be selected to minimize undesired backflow. The implant takes into account possible interruptions in blood flow. Such interruptions may include hemorrhaging and stroke. A one-way valve is provided in the arterial conduit of the device which prevents a backflow from the vein to the artery.

The implant is preferably made of a light, flexible or semiflexible material which would not subject the receiving organism to various implant-related traumas. Such traumas include blood clotting on the surface of the implant, puncturing of the vasculature by the implant and infection, etc.

The device in some embodiments may serve as a pump to increase venous blood flow to an organ such as the liver. In a cirrhotic liver, for example, the device according to the invention serves to decompress the fluid flow namely excessive arterial pressure by diverting flow to a lower pressure fluid path, thereby increasing in the portal vein and the hepatic vein to improve the filtering function of the liver. High volume arterial flow thus does not inhibit portal flow.

It is an object of this invention to provide a method and apparatus for relieving hypertension in the liver, such as may exist in a cirrhotic liver, by reducing the pressure of blood delivered to the liver from the hepatic artery. To this end, the device may be used to divert blood from the hepatic artery to the portal vein proximal of the liver. An advantage of such arrangement is that pressure on the liver is relieved allowing the liver to repair itself in due course.

It is a further object of the present invention to stimulate portal vein blood flow. An advantage is elimination of hepatic encephalopathy as a result of increased portal vein blood flow. A further advantage is the oxygenation of the venous blood by the infusion of oxygen-rich arterial blood from the hepatic artery.

Another object of this invention is to provide a method and apparatus for mixing blood diverted from the hepatic artery with blood in the portal vein proximal of the liver. The portal vein has a larger diameter than the hepatic artery and it can readily dissipate or decompress the added flow from the artery.

Another object of the invention is to provide an implant for diverting blood from the hepatic artery to the portal vein such that hypertension of the liver is reduced. By diverting blood through an implant and forming a junction through which diverted blood enters the portal vein within the implant, hypertension of the vein due to the angularly added arterial blood flow is eliminated.

Another object of the invention is to provide an implant for diverting blood flow from the hepatic artery to the portal vein, the implant including an arterial conduit disposed within a portal vein conduit and having an outlet nozzle including a one-way valve within the nozzle. An advantage of placing the arterial conduit within the portal vein conduit is that arterial blood flow may be directed distally within the portal vein thereby reducing turbulence and possible interference with normal venous blood flow. Blood introduced from the high pressure source (the artery) into the low pressure vessel (the veins) will not cause hypertension of the vein. Additionally, thorough mixing of the arterial and venous blood is encouraged.

Inclusion of a back-flow or one-way valve prevents venous blood from contaminating arterial blood in the event of an arterial blood pressure drop or a back-flow of venous blood.

In a particular embodiment of the invention the implant is formed of a flexible polymer fabric tube. The material is of such a nature that it inhibits damage to blood cells. It is strong and compatible with the organism and is not subject to shear and related stress failure. In other embodiments the implant may be formed of a flexible plastic tube. Such material has similar advantages to those of the polymer fabric tube.

In a further particular embodiment a plurality of arterial conduits are provided such that the hepatic artery may be variously tapped according to the requirements of the particular application. In this way, blood flow diversion is varied for each patient. Such arrangement is useful in providing treatment to patients with varying degrees of liver disorder, such that each patient requires a different amount of arterial blood to be diverted from the liver.

While the principal application appears to be in the treatment of liver conditions related to cirrhosis, a device according to the invention may be used in applications other than as a shunt from the hepatic artery. For example, the device may be used for diverting and mixing blood flow to other organs, such as the lungs. In particular, such a device may be used to connect veins to one another, such as the vena cava and the portal vein in a porta-caval shunt.

Other objects, features, and advantages of this invention will become more apparent. For instance, the present invention may find application in the treatment of pulmonary hypertension.

BRIEF DESCRIPTION OF THE DRAWINGS

The novelty and significance of the present invention will be more fully appreciated after referring to the following detailed description and attached drawings in which:

FIG. 1 is a diagram of the implant shown in connection with a vascular and hepatic system;

FIG. 2 is a top view of the implant;

FIG. 3 is a cross-section of the implant taken along line 3—3 in FIG. 2; and

FIG. 4 is a cross-section of the implant taken along the line 4—4 in FIG. 3.

DETAILED DESCRIPTION OF THE SPECIFIC EMBODIMENTS

According to the invention an implanted device allows for the coupling of blood vessels to one another. In a particular illustrative embodiment the hepatic artery may be constricted or ligated, and arterial blood is mixed in the portal vein proximal of the liver through the device to boost venous blood flow. Decreased flow through the hepatic artery decreases pressure to the liver, reducing the possibility of liver hypertension. Thus, a damaged liver is believed to be more apt to heal. In addition, according to the invention the venous blood in the portal vein is oxygenated by the mixing of diverted arterial blood from the hepatic artery with the venous blood prior to introduction into the liver. The liver thus receives oxygen through an alternative route from the hepatic artery. In some applications it may be preferred that the hepatic artery be ligated and all arterial flow be diverted through the portal vein.

Referring now to FIG. 1, a vascular/hepatic system having an implant 27 for reducing hypertension is shown. The hepatic artery 11 and portal vein 26 are shown proximal of the liver 15. Direction of blood flow is indicated by arrows within the conduits. Blood flow from the hepatic artery 11 and blood flow from the portal vein 26 generally merge within the liver 15 to form a blood source for the hepatic vein 16. Excessive arterial pressure is believed to block venous blood flow through the liver 15.

According to the invention, the portal vein 26 is divided into sections 10 and 14 and a portal vein conduit 17 is shown inserted between the sections 10 and 14. An arterial conduit 12 joins the portal vein conduit 17 at a junction 22. The arterial conduit 12 may include a plurality of branches 13, depending upon the desired reduction of blood flow from the hepatic artery 11 to the liver 15.

Referring to FIG. 2, the portal vein conduit 17 of the implant 27 includes a proximal (upstream) portal vein inlet 19 (FIG. 2) and a distal (downstream) portal vein outlet 20; the arterial conduit 12 includes a proximal arterial conduit inlet 18.

An outlet nozzle 21 of the arterial conduit 12 is disposed within the portal vein conduit 17 at junction 22 as is indicated in FIGS. 3 and 4. In one embodiment of the present invention implant 27 is made of a flexible polymer fabric tube. One such material is described in U.S. Pat. No. 3,986,828. Alternatively, the implant could be made of a medical quality elastomeric tube, such as expanded polytetrafluoroethylene. In such embodiments, the arterial conduit 12 and the portal vein conduit 17 may be joined at junction 22 by stitching, gluing, or other such methods.

The arterial conduit 12 is reduced in diameter at its distal end to form the outlet nozzle 21 (FIGS. 3 and 4). The nozzle 21 is secured within the portal vein conduit 17 by two flaps or wings 25, the flaps 25 being secured by stitching, gluing, or other such methods to an inside wall of the portal vein conduit 17.

The arterial conduit outlet nozzle 21 may be formed in the implant material by tapering the arterial conduit 12 progressively to form the nozzle. In fabric, such tapering may be accomplished by diagonal stitching on either side of the desired nozzle location. The stitching extends from the tip of the nozzle toward edges of the arterial conduit. In this way, the two triangular flaps or wings 25 are formed. An advantage of using a flexible material for the arterial conduit 12 is that the outlet nozzle 21 forms a one-way valve for preventing back-flow of venous blood into the arterial vascular system in the unlikely event of a reversal in pressure differential. A negative pressure in the one-way valve causes the outlet nozzle 21 to collapse. This seals off the nozzle 21 and prevents back-flow of venous blood through the one-way valve. The presence of venous blood about the outlet nozzle 21 causes a high exterior pressure on the outlet nozzle that keeps the one-way valve closed until a positive pressure is restored in the hepatic artery 11.

When installing the implant 27 into the hepatic/vascular system the receiving organism is opened to expose the hepatic artery 11 and the portal vein 26 near the liver 15. The portal vein is clamped at each of the two sections 10 and 14 to prevent hemorrhaging. The portal vein is then bisected.

The implant is inserted between the two sections 10 and 14 of the portal vein 26 and secured in place by suturing or otherwise attaching the two vein sections 10 and 14 to the implant 27. The portal vein conduit 17 should be placed with the arterial conduit outlet nozzle 21 angularly disposed within the portal vein conduit 17 in the distal flow direction. The proximal portal vein inlet 19 should be joined to portal vein section 10, and the distal portal vein outlet 20 should be joined to portal vein section 14.

The hepatic artery 11 is clamped proximally of an incision position to cut blood flow during attachment of the arterial conduit. One or more proximal arterial conduit inlets 18 are secured to the various branches of the hepatic artery 11 by sutures or other such means. The hepatic artery into the liver is wholly or partially ligated. The vein sections 10 and 14 and the hepatic artery 11 are then unclamped to restore normal venous and arterial blood flow. Blood is diverted from the hepatic artery to the portal vein. Reduced blood pressure/blood flow to the liver should reduce liver hypertension and foster the healing process in the damaged liver.

It is important to provide a flexible implant that will not damage blood cells flowing through the implant. The implant should not cause infection or excessive perterbation of the fragile body tissues surrounding it.

Once implanted, the present invention decompresses the hepatic artery by drawing off a flow of high-pressure arterial blood and mixing that flow with a low-pressure blood flow in the portal vein. The ratio of mixing can be controlled by the relative size of the nozzle. The arterial blood may also serve as a motive force for pumping the venous blood. Hypertension of the portal vein is prevented by introducing the arterial blood flow into the portal vein nearly axially such that even decompression is encouraged.

In other embodiments of the invention, the arterial conduit could be flush with the portal vein conduit rather than internally disposed within the portal vein conduit. Such an arrangement would allow the arterial blood flow introduced into the venous flow to stimulate the venous flow.

In another embodiment of the invention, the flexible material from which the conduits are formed could encourage blood vessel and other tissue growth therealong. Thus, the implant would be covered with blood vessels and would be securely part of the body. The possibility of failure due to separation of the conduit from the blood vessel would thus be nonexistent.

A further embodiment of my invention contemplates using the conduit for the treatment of pulmonary hypertension. In such application, blood flow in the lungs would be diverted.

The scope of the disclosed invention should be limited only by the breadth of the following claims.

I claim:

1. A method for reducing hypertension of a liver having a hepatic artery, comprising:
    ligating the hepatic artery into the liver;
    diverting the blood from the hepatic artery proximal of the liver by means of an arterial conduit formed of polymer fabric to a portal vein conduit formed of a polymer fabric;
    joining flow through the arterial conduit to flow through the portal vein conduit at a junction formed of polymer fabric;
    discharging said joined arterial blood flow and portal vein blood flow proximal of the liver, said portal vein conduit being inserted in said portal vein proximal of the liver, thereby to reduce blood pressure in the liver.

2. The method of claim 1 further comprising: mixing in a controlled ratio arterial blood diverted from said hepatic artery with venous blood from said portal vein at an arterial conduit blood discharge nozzle disposed within said portal vein conduit.

* * * * *